(12) United States Patent
Masson

(10) Patent No.: US 8,535,313 B1
(45) Date of Patent: Sep. 17, 2013

(54) BONE PLATE WITH SUTURE RETAINING ELEMENTS

(76) Inventor: Marcos V. Masson, Houston, TX (US)

( * ) Notice: Subject to any disclaimer, the term of this patent is extended or adjusted under 35 U.S.C. 154(b) by 173 days.

(21) Appl. No.: 13/047,516

(22) Filed: Mar. 14, 2011

(51) Int. Cl.
*A61B 17/56* (2006.01)

(52) U.S. Cl.
USPC ............... 606/70; 606/71; 606/286; 606/293; 606/232

(58) Field of Classification Search
USPC ....... 606/70–71, 280–299, 74, 902, 232–233, 606/103
See application file for complete search history.

(56) References Cited

U.S. PATENT DOCUMENTS

| | | | |
|---|---|---|---|
| 6,096,040 A | 8/2000 | Esser | |
| 7,604,657 B2 | 10/2009 | Orbay et al. | |
| 7,731,718 B2 * | 6/2010 | Schwammberger et al. | ... 606/71 |
| 2004/0225291 A1 * | 11/2004 | Schwammberger et al. | ... 606/71 |
| 2006/0100623 A1 | 5/2006 | Pennig | |
| 2006/0241617 A1 | 10/2006 | Holloway et al. | |
| 2008/0306510 A1 * | 12/2008 | Stchur | ............ 606/232 |
| 2009/0225291 A1 * | 9/2009 | Mori et al. | ........ 355/30 |
| 2009/0264936 A1 * | 10/2009 | Gonzalez-Hernandez et al. | ............. 606/286 |
| 2009/0326591 A1 | 12/2009 | Spencer | |

* cited by examiner

*Primary Examiner* — Todd Manahan
*Assistant Examiner* — Marcela I Shirsat
(74) *Attorney, Agent, or Firm* — Egbert Law Offices, PLLC

(57) ABSTRACT

A bone plate has a body with an outer surface and a bone-contacting surface with a channel formed at a periphery of the body, and a suture member having an end slidably received in the channel. The suture member has an end extending outwardly of the channel. The channel is formed along at least one side of the body. The suture member includes a retainer member received in the channel, a shank extending through the channel, and a loop member affixed to the end of the shank opposite the retainer member. The loop member has a shape suitable so as to allow a suture to be affixed thereto. The body has a slot communicating with the channel and opens at the outer surface so as to allow the suture member to be inserted into the channel.

4 Claims, 2 Drawing Sheets

BONE PLATE WITH SUTURE RETAINING ELEMENTS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates broadly to surgical devices. More particular, the present invention relates to orthopedic bone plates, particularly for fracture fixation. Additionally, the present invention relates to orthopedic bone plates having suture connectors, loops, receptacles or members thereon.

2. Description of Related Art Including Information Disclosed Under 37 CFR 1.97 and 37 CFR 1.98.

The proximal humerus comprises the upper portion of the humerus (i.e. upper arm of the human body) and forms a portion of the shoulder joint. Fractures of the proximal humerus typically result from traumatic injury, such as sporting accidents, and can be frequent with age due to bone loss. Fractures of the proximal humerus are treated by exposing the fracture site and reducing the bone fracture and then placing a plate onto the bone to fixate the fracture for healing in the reduced position. Reducing the fracture includes realigning and positioning the fractured portions of the bone to their original position or similar stable position. Fixating the fracture includes positioning a plate over the fractured portion and then securing the plate onto the fractured bones and adjacent non-fractured bones with bone screws. Commonly, after a fracture, there exists disassociated tuberosities at the proximal portion of the humerus. Tuberosities are pieces of bone with tendons attached. The bone is weak, but the insertion points of the tendons are very strong. The accepted way to reattach the bone for healing is to use suture material to stitch into the insertion point of the tendon and pull down to anchor the bone with the suture.

Humeral plates often include suture holes at which suture material, e.g. braided cord or wire suture, can secure the tuberosity to the plate. The suture holes are generally circular holes extending transverse to the longitudinal axis of the plate. For example, the Philos™ plate by Synthes includes multiple suture holes displaced around the plate which extend between the bone contacting and lower plate surfaces. Because one opening of each suture hole is even with the bone-contacting surface, access to or egress from the holes is impeded.

Various patents have issued and patent publications have published relating to such bone fixation plates. For example, U.S. Patent Publication No. 2006/0100623, published on May 11, 2006 to D. Pennig, describes a system for fixation of bone fractures. In particular, this is a system for improving the fixation of proximal fractures of the humerus. This system includes at least one humeral nail that is inserted in a humeral shaft. There are several and proximal transversal holes for the passage of corresponding locking screws. At least one screw of the locking screws has a screw head and a screw body. An intermediate plate element is inserted between the screw head and the bone cortex surface so that the head is abutting against the plate. The intermediate plate element is slightly bent to adhere substantially to the bone cortex surface. The intermediate plate element has a couple of elongated arm portions that are inserted in an astride position on the screw body before the final fastening of the screw head.

U.S. Patent Publication No. 2006/0241617, published on Oct. 26, 2006 to Holloway et al., provides a bone plate with suture loops. The suture loops are flexible and formed of a strong suture material. The suture loops may have various shapes, forms and configurations. These suture loops are provided on the bone plate in locations depending on the characteristics of the fractured bone or bone segment. Preferably, the suture loops are attached to a surface of the bone plate. The suture loops serve to receive a strand of suture for fixation of soft tissue to the bone plate.

U.S. Pat. No. 7,604,657, issued on Oct. 20, 2009 to Orbay et al., teaches a bone fixation plate with complex suture anchor locations. This fracture fixation system includes a plate having a first suture anchor location having an opening at the upper surface of the plate, an opening at the proximal end of the plate, and an opening at the anterior side of the plate. First and second suture pathways are defined which cross within the plate. The first and second suture pathways include a common opening. A second suture anchor location on the plate has an opening at the upper surface of the plate, an opening at the proximal end of the plate, and an opening at the posterior side of the plate so as to define third and fourth suture pathways which cross within the plate. The third and fourth suture pathways also share a common opening. Each suture anchor location is capable of providing a hold for sutures from multiple approaches so as to secure tuberosities relative to the plate.

U.S. Pat. No. 6,096,040, issued on Aug. 1, 2000 to R. D. Esser, discloses an upper extremity bone plate. The first bone plate is configured and arranged to match the contour of a healthy unfractured proximal humerus. The bone plate includes an elongate shaft portion and a head portion. The shaft portion is adapted for receiving bone screws to fix the bone plate to a shaft of a humerus. The head portion includes a first head section and a second head section with an obtuse angle defined therebetween. The first and second head sections extend laterally away from a longitudinal axis of the shaft portion in generally opposite directions. The second head section is configured and arranged with a lateral portion to secure multiple fractures of a head of proximal humerus while extending laterally adjacent to the biceps tendon to preserve the tendon.

U.S. Patent Publication No. 2009/0326591, published on Dec. 31, 2009 to E. E. Spencer, teaches a system and method to position and secure fractured bones. In particular, this system is intended for reducing a proximal fractured humerus and includes a fracture reduction plate and an elongated pin including a plurality of threads. The elongated pin is configured to be inserted through the fracture reduction plate and engage with a humeral head. The fracture reduction plate is placed on the fractured humerus and provisionally secured. Sutures may be used to guide the fracture reduction plate into place on the fractured humerus. Next, the elongated pin is engaged with the humeral head at a superior angle relative to the humerus and the fracture is reduced. The elongated pin may be used to push the humeral head in a superior direction while pulling on the humeral head using the sutures. The fracture reduction plate can then be secured to the humerus and the elongated pin removed.

One of the difficulties associated with these prior art references is that the suture receptacles on the bone plate are generally in a fixed location. Depending upon the nature, shape, and size of the fracture of the proximal humerus, the desired locations for the suture retainers may significantly vary from that of the fixed positions of the prior art. As such, it is desirable to offer a bone plate in which the suture receptacle can be manipulated and positioned in a continuously variable manner around a surface of the bone plate. As a result, a surgeon would be able to properly position the suture receptacles in the most desirable position so as to achieve the proper suturing of the tuberosities.

It is an object of the present invention to provide a bone plate in which the suture receptacles can be positioned at various desirable locations around the bone plate.

It is another object of the present invention to provide a bone plate in which the suture receptacles can be locked in their desired positions prior to suturing.

It is another object of the present invention to provide a bone plate in which each of the suture receptacles offers a maximum amount of space so as to allow the suture to be easily introduced therein and therethrough.

It is still another object of the present invention to provide a bone plate with suture receptacles which is easy to use, relatively inexpensive and easy to manufacture.

These and other objects and advantages of the present invention will become apparent from a reading of the attached specification and appended claims.

BRIEF SUMMARY OF THE INVENTION

The present invention is a bone plate comprising a body having an outer surface and a bone-contacting surface with a channel formed thereof at a periphery of the body, and a suture member having an end slidably received in channel. The suture member has an end extending outwardly of the channel.

The channel is formed along at least one side of the body and positioned between the outer surface and the bone-contacting surface. The body has a slot communicating with channel. The slot opens at the outer surface. The slot has a size suitable for allowing the suture member to be inserted into the channel. The body has a forward end and a rearward end. The slot extends between the channel and the outer surface at the forward end. The body also has a plurality of holes formed therein. The plurality of holes extend so as to open at the outer surface and the bone-contacting surface. This plurality of holes are suitable for allowing bone screws to be inserted therethrough.

The channel has a generally T-shape. In particular, the channel has a first portion that opens at the side of the body. This first portion extends in generally parallel relation to the outer surface of the body. The channel also includes a second position that extends transverse to the first portion and is in spaced relationship to the side. The second portion has a width that is greater than a width of the first portion.

The suture member includes a retainer member received in the channel, a shank extending through the channel, and a loop member affixed at end of the shank opposite the retainer member. The retainer member is a spheroid member positioned in the second portion of the channel inwardly of the periphery of the body. This spheroid member is of a non-uniform radius such that the spheroid member is lockable in the channel with a rotation of the spheroid member. The shank has a width that is less than a width of the first portion of the channel. The loop member has a shape suitable so as to allow a suture to be affixed thereto. This loop member has an interior opening formed therein. The interior opening has a size suitable for allowing the suture to pass therethrough. The loop member has a generally triangular shape with a narrow end of the triangular shape affixed to the shank and a wide end extending outwardly therefrom.

DETAILED DESCRIPTION OF THE INVENTION

Figure 1:
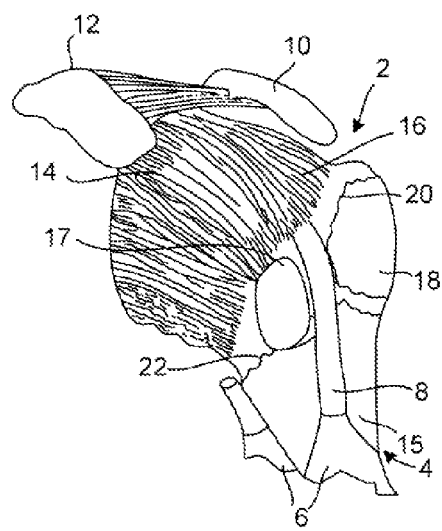
FIG. 1 is a side elevational view of a left shoulder joint as seen from an anterior orientation.

Referring to FIG. 1, there is shown an anterior view of the left shoulder joint. The shoulder joint 2 generally includes a proximal humerus 4, a bicep muscle 6, a bicep tendon 8, an acromion process 10, a coracoid process 12 and an articular capsule 14. Proximal humerus 4 includes shaft 5, head 16, including the lesser tuberosity 17 and the greater tuberosity 18. Fractures of the proximal numerous typically separate the humerus head 16 from the humerus shaft 15 and, at times, also separates the greater tuberosity 18 and the lesser tuberosity 17 from head 16. These fractures are depicted, in part, by vertical fracture line 20 extending about the greater tuberosity 18 and by horizontal fracture line 22 extending across of the humeral shaft 15. The bone plate of the present invention, as shown in FIGS. 2-7, is adapted for a reduction and internal fixation of all fractures of the proximal humerus and especially adapted for reduction and internal fixation of three and four part fractures of the proximal humerus 4.

Figure 2:
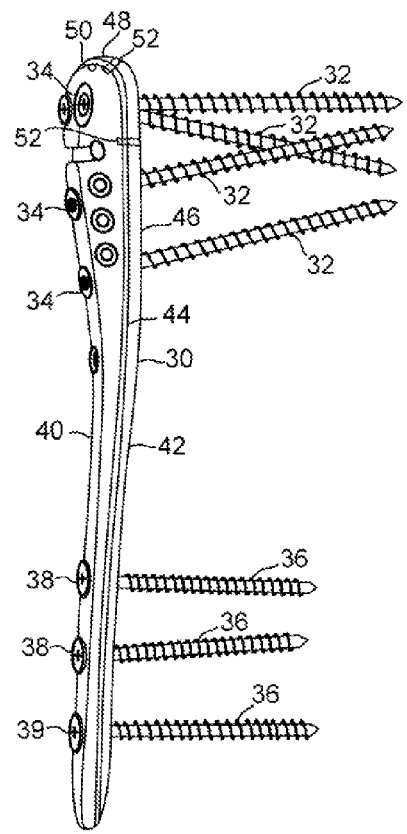
FIG. 2 is a side elevation view of bone plate in accordance with the teachings of the present invention.

FIG. 2 is a side view of the bone plate 30 with self-locking screws 32 inserted into proximal locking screw holes 34 and self-tapping compression screws 36 inserted into this distal compression screw holes 38. As can be seen in FIG. 2, the self-tapping locking screws 32 are inserted through the proximal locking screw holes at an angle.

The bone plate 30 has an outer surface 40 and a bone-contacting surface 42. A channel 44 is formed along a periphery 46 of the bone plate 30. The channel 44 will extend along the sides of the bone plate 30 and around the frontal end 48. A slot 50 is formed on the outer surface 40 at the frontal end 48. Slot 50 allows the suture retainer 52 to be inserted into the channel 44. FIG. 2 show that suture retainers 52 are positioned in desired locations relative to the channel 44.

Figure 3:
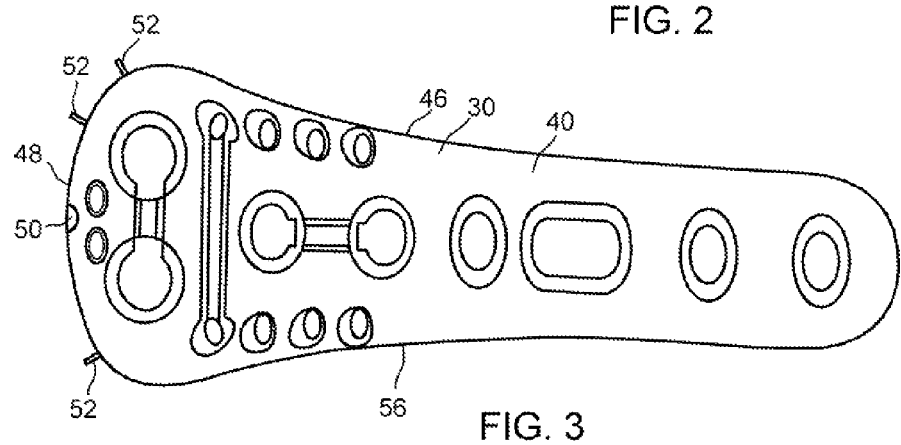
FIG. 3 is a plan view of the bone plate in accordance with the teachings of the present invention.

FIG. 3 shows a plan view of the bone plate 30 of the present invention. In particular, in FIG. 3, it can be seen that the outer surface 40 of the bone plate 30 has a frontal end 48. Suture retainers 52 extend radially outwardly at the frontal end 48. It should be noted that, within the concept of the present invention, the suture retainers 52 can be positioned anywhere along the sides of the body of the bone plate 30. As such, the suture retainers 52 can be movable to any desired location along the surfaces.

FIG. 3 shows that there is a slot 50 formed at the frontal end 48 of the bone plate 30. Slot 50 is illustrated as having a generally semi-circular opening. The slot 50 will form a slot extending to the channel 44. As such, the retaining end of each of suture retainers 52 can be introduced into the channel 44 and, hence, moved to the desired positioning locations.

Figure 4:
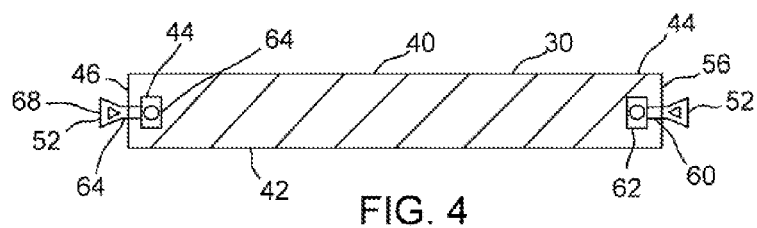
FIG. 4 is a cross-sectional view of the bone plate of the present invention showing, in particular, the suture retainer members.

FIG. 4 is a cross-section review of the body of the bone plate 30. As can be seen, the bone plate 30 has a outer surface 40 and a bone-contacting surface 42. The bone plate 30 has a first side 46 and a second side 56. In FIG. 4, it can be seen that the channel 44 extends around the bone plate 30 and opens at the sides 46 and 56.

The channel 44 includes a first portion 60 that extends so as to open at the sides 46 and 56. The first portion 60 will extend in generally parallel relationship to either the outer surface 40 or the bone-contacting surface 42. The channel 44 also includes a second portion 62 that communicates with the first portion 60. The second portion 62 is illustrated as having a width greater than the width of the first portion 60. The second portion 62 is spaced slightly from the sides 46 and 56 of the bone plate 30.

Previously, the formation of channel 44 within the bone plate 30 would have been considered an impossible manufacturing task when the body 30 must be integrally formed of a strong steel material. However, with the advent of electron beam melting, it is possible to configure such a shape so as to accommodate the fixed positioning of the suture retainers 52 within such channels. Electron beam melting is a technology for manufacturing objects, such as implants and fixation instruments. In electron beam melting, an electron beam is directed into a powder. The powder is preferably comprised of materials that make an osteoconductive/osteinductive implant and fixation instrument after electron beam melting. The electron beam has an extremely high temperature. As a result, the materials in the powder melt upon contact. All of the objects made during this electron beam melting process are made from the inside out by melting and cooling layer-upon-layer of the object upon itself. The temperature of the electron beam can be adjusted by adjusting the intensity and magnetic fields that control the direction and diameter of the electron beam. The manufacture of the bone plate 30 by electron beam melting ensures that the density is constant, the purity of the material is high and the contour of the bone place produced can be controlled with high levels of detail. As such, through this electron beam melting process, the channel 44 can be effectively and strongly formed at to the sides 46 and 56 of the bone plate 30.

In FIG. 4, it can be seen that the suture retainers 52 extend outwardly from the sides 46 and 56. Each of the suture retainers 52 includes a retainer member 64, a shank 66 and a loop member 68. The retainer member 64 is a generally spheroid member. The retainer member 64 is illustrated as positioned in the second portion 62 of the channel 44. Ideally, the spheroid member will have a non-uniform radius. As such, when a rotation force is applied to the loop member 68 and the shank 66, the retainer member 64 can be rotated so as to effectively "wedge" within this second portion 62 of the channel 44.

The shank 66 will extend through the first portion 60 of the channel 44. The shank 66 has one end affixed to the retainer member 64. The shank 66 has a diameter that is slightly less than a width of the first portion 60 of the channel 44. As such, the suture retainer 52 can be effectively moved along the channel 44 to the desired location.

The loop member 68 is affixed to an end of the shank 66 opposite the retainer member 64. The loop member has an opening therein suitable for allowing the suture to be introduced therein and therethrough. As such, the sutures can be effectively secured to the loop member 68.

Figure 5:
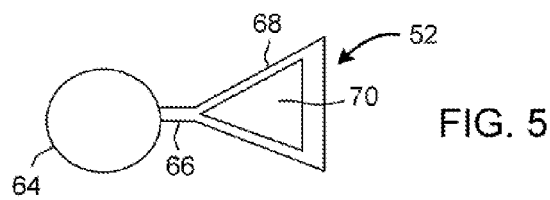
FIG. 5 is a detailed view of a single suture retainer member as use with the present invention.

FIG. 5 is an isolated view of the suture retainer 52. The suture retainer 52 has a retainer member 64, shank 66 and a loop member 68. The retainer member 64 is illustrated as being a spheriod member. It can be seen in FIG. 5 that the retainer member 64 has a non-uniform radius. The shank 66 has one end connected to the retainer member 64. The loop member 68 is connected to an opposite end of the shank 66. In FIG. 5, it can be seen that the loop member 68 has a generally triangular shape with a narrow end affixed to the shank 66 and a wide end extending outwardly therefrom. The interior opening 70 is suitable for allowing the suture to be introduced therein. The sharp corners associated with the triangular-shaped interior opening 70 can serve to effectively engage with the suture so as to fix the position of the suture within this opening 70.

Figure 6:
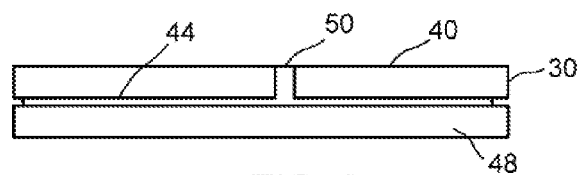
FIG. 6 is a front end view of the bone plate of the present invention.

FIG. 6 is a frontal view of the body 30. As can be seen, there is a slot 50 formed at the frontal end 48 of body 30. Slot 50 opens at the outer surface 40 of the body 30 and also has an end opening to the channel 44.

In normal use, the slot 50 will have a size suitable so as to allow the retainer member 64 to be inserted therein. As such, the retainer member 64 can slide downwardly in the slot 50 to the channel 44. Once the retainer member 64 is positioned in the channel 44, it can be slidably moved along the channel 44 to the desired location. Once the retainer member 64 is in the desired position, a rotational force applied to either the loop member 68 and/or shank 66 will cause the retainer member 64 to rotate so as to wedge properly within the channel 44 at this desired position.

Figure 7:
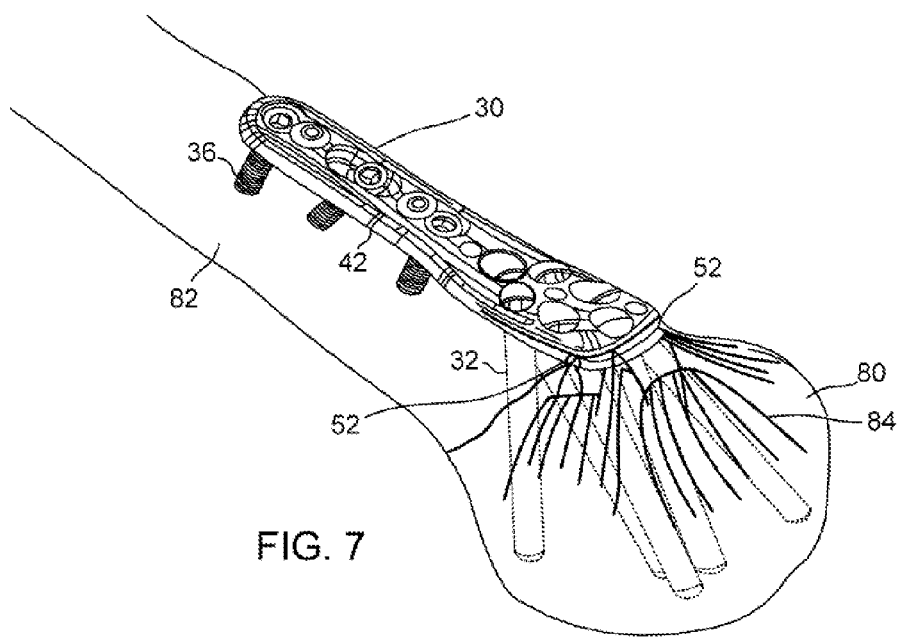
FIG. 7 is an illustration of the bone plate of the present invention as applied to the humeral bone.

FIG. 7 shows the attachment of the bone plate 60 to the humeral head 80 and the humeral shaft 82. As can be seen, the various bone screws 32 and 36 have been driven into the respective locations on the humeral head 80 on the humeral shaft 82. As such, the bone contacting surface 42 of the bone plate 30 is effectively positioned onto the surfaces of the humeral head 80 and the humeral shaft 82. The suture retainers 52 are positioned adjacent the forward end of the bone plate 30. As can be seen, the various sutures 84 are received by the suture retainers 52. The sutures 84 assure that the tuberosities are properly positioned.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A bone plate apparatus comprising:
   a body having an outer surface and a bone-contacting surface, said body having a peripheral surface extending between said outer surface and said bone-contacting surface, said body having a channel formed into said peripheral surface in a location between said outer surface and said bone-contacting surface, said channel extending along an entire length of said peripheral surface; and
   a suture retainer having an end slidably received in said channel, said suture retainer having an end extending outwardly of said channel, said end of said suture retainer being rotatable in said channel so as to lock a position of said suture retainer with respect to said body.

2. The bone plate apparatus of claim 1, said body having a slot communicating with said channel and opening at said outer surface, said slot having a size suitable for allowing said suture retainer to be inserted into said channel.

3. A bone plate apparatus comprising:

a body having an outer surface and a bone-contacting surface, said body having a channel formed thereof at a peripheral surface of said body, said channel having a first portion extending parallel to said outer surface and having a first end opening at a side of said body between said outer surface and said bone-contacting surface, said channel having a second portion at a second end of said first portion, said second portion of said channel having a width greater than a width of said first portion; and a suture retainer having a first end positioned in said second portion of said channel and a second end extending outwardly of said body, said suture retainer comprising:

a retainer member positioned in said second portion of said channel;

a shank extending through said first portion of said channel, said shank having an end affixed to said retainer member; and a loop member affixed to an opposite end of said shank, said loop member extending outwardly of the side of said body, said loop member having an interior opening formed therein, said interior opening suitable for allowing the suture to pass therethrough, said loop member having a generally triangular shape with a narrow end of said triangular shape affixed to said shank and a wide end of said triangular shape extending outwardly therefrom, said interior opening having sharp corners in said generally triangular shape, said retainer member being a spheroid member positioned in said channel, said spheroid member having a non-uniform radius such that said spheroid member is lockable in said channel with a rotation of said spheroid member.

4. The bone plate apparatus of claim 3, said body having a slot communicating with said channel and opening at said outer surface, said slot having a size suitable for allowing said suture member to be inserted into said channel.

* * * * *